United States Patent [19]
Halenbeck et al.

[11] Patent Number: 5,491,065
[45] Date of Patent: Feb. 13, 1996

[54] MONOCLONAL ANTIBODIES THAT BIND TO AND NEUTRALIZE DIMERIC BUT NOT MONOMERIC HUMAN M-CSF AND METHODS OF USE THEREOF FOR DETECTION OF DIMERIC M-CSF

[75] Inventors: Robert F. Halenbeck, San Rafael; Kirston E. Koths, El Cerrito; Joseph W. Wrin, San Francisco, all of Calif.

[73] Assignee: Cetus Oncology Corporation, Emeryville, Calif.

[21] Appl. No.: 156,862

[22] Filed: Nov. 19, 1993

Related U.S. Application Data

[63] Continuation of Ser. No. 919,500, Jul. 24, 1992, abandoned, which is a continuation of Ser. No. 310,042, Feb. 10, 1989, abandoned.

[51] Int. Cl.$^6$ .......................... G01N 33/53; C07K 16/24; C12N 5/20
[52] U.S. Cl. .................. 435/7.1; 435/240.27; 435/172.2; 435/70.21; 530/388.23; 530/389.2; 530/388.15
[58] Field of Search ........................... 530/388.23, 389.2, 530/388.15; 435/240.27, 172.2, 70.21, 7.1

[56] References Cited

U.S. PATENT DOCUMENTS

| | | |
|---|---|---|
| 4,504,586 | 3/1985 | Nicolson . |
| 4,929,700 | 5/1990 | Halenbeck et al. . |

OTHER PUBLICATIONS

Ralph, et al., 1987, Molecular Basis of Lymphokine Action, (Webb, et al. Eds.), Humana Press, pp. 295–311.
Wang, et al., 1983, Journal of Cellular Biochemistry, 21:263–275.
Daugherty, et al., 1991, Nucleic Acids Research, 19(9):2471–2476.
Verhoeyen, et al., 1988, Science, 239:1534–1536.
Bieber et al. "In Vitro Sensitization for the Production of Monoclonal Antibodies", In *Human Hybridomas*, Strelkauskas Ed. Dekker 1987.
Campbell *Monoclonal Antibody Technology* 1984, Elsevier Press.
Stanley et al. J. Immunol. Methods 42:253–281 1981.
Lokeshwar et al. J. Immunol. 141:483–488 15 Jul. 1988.
Co et al., Nature 351:501–2, 1991.
Halenbeck et al. Bio/Technology 7:710–715, 1989.

*Primary Examiner*—Paula K. Hutzell
*Attorney, Agent, or Firm*—Philip L. McGarrigle; Kenneth Barovsky; Robert P. Blackburn

[57] ABSTRACT

Monoclonal antibodies that bind to an apparent conformational epitope associated with recombinant or native dimeric M-CSF with concomitant neutralization of biological activity, which monoclonal antibodies are substantially unreactive with biologically inactive forms of M-CSF including monomeric and chemically derivatized dimeric M-CSF, are described. Methods of using the antibodies in assays for detection of dimeric M-CSF are also described.

10 Claims, 3 Drawing Sheets

MONOCLONAL ANTIBODIES THAT BIND TO AND NEUTRALIZE DIMERIC BUT NOT MONOMERIC HUMAN M-CSF AND METHODS OF USE THEREOF FOR DETECTION OF DIMERIC M-CSF

CROSS REFERENCE TO RELATED APPLICATIONS

This application is a continuation of application Ser. No. 07/919,500, filed Jul. 24, 1992, now abandoned, which is a continuation of application Ser. No. 07/310,042, filed Feb. 10, 1989, now abandoned.

This application is related to U.S. patent applications Ser. Nos. 07/170,556 (now abandoned), U.S. Pat. No. 4,847,201) filed on Mar. 21, 1988 and Feb. 9, 1988, respectively.

TECHNICAL FIELD

The present invention relates generally to the field of immunology, and particularly to monoclonal antibodies to Macrophage Colony-Stimulating Factor (M-CSF). More specifically, the invention relates to neutralizing monoclonal antibodies to M-CSF that bind to an apparent conformational epitope associated predominately with dimeric, but not monomeric M-CSF.

BACKGROUND ART

Over the past decade, several proteins have been identified that affect the multi-cell lineage differentiation of hematopoietic cells. These proteins cause a common set of pluripotent stem cells, which reside predominantly in the bone marrow, to differentiate into red cells, neutrophils, basophils, eosinophils, monocytes, platelets, and lymphocytes. Such proteins were initially identified by their ability to support clonal growth of hematopoietic progenitor cells in semisolid media, and as a result they are referred to as hematopoietic colony-stimulating factors, or CSFs.

In those systems which have been most studied, human and mouse, CSFs have been identified and characterized by the types of cells whose differentiation and proliferation they appear to enhance. Two CSFs are relatively lineage specific, and have ascribed to them the names of the cells that they produce. For instance, granulocyte-CSF (G-CSF) generates mostly neutrophilic granulocytes, and macrophage CSF (M-CSF) generates largely macrophages. In contrast to these two CSF's, multi-CSF (also known as interleukin-3 or IL-3) produces colonies composed of many different cell lineages. Lastly, granulocyte-macrophage-CSF (GM-CSF) effects the production of neutrophilic granulocytes, macrophages, and eosinophils, as well as other cell types. It is thought that G-CSF and M-CSF are responsible for the growth and proliferation of temporaxily late progenitor cells already committed to the production of granulocytes, and macrophages, respectively. In contrast, GM-CSF is thought to interact with progenitor cells produced early during hematopoiesis that are capable of differentiating into several different cell types; neutrophils, eosinophils, or monocytes. Similarly, the multiplicity of activities attributable to IL-3 is believed to be a result of its capacity to support the growth of cells from relatively early pluripotent progenitor cells to mature hematopoietic cells of different lineages.

Because CSFs are thought to have significant clinical applications, considerable effort has been expended to identify sources of CSFs, and to develop ways of purifying the molecules from bodily fluids or cell culture supernatants, where they may be present at very low levels. Consequently, in order to increase the mounts of CSFs available for clinical studies, the DNA sequences that encode the various CSFs have now been identified, cloned into suitable expression vehicles, and the recombinant proteins generated therefrom characterized with regard to their physical properties and their biological activities. Concomitantly, antibodies have been, and continue to be generated that react with the various CSFs that can be used as tools to facilitate their isolation and purification, as well as having therapeutic or diagnostic applications.

SUMMARY OF THE INVENTION

An object of the instant invention is a description of monoclonal antibody that binds predominately to dimeric but not monomeric forms of both recombinant and naturally occurring M-CSF, and methods of using the monoclonal antibody.

A second object of the invention is a description of monoclonal antibody that binds to an apparent conformational epitope associated with dimeric forms of M-CSF, which epitope is in or near the region responsible for the biological activity of M-CSF as revealed by the neutralizing capacity of the antibody, and is located between amino acids 4 and 150 of native M-CSF.

A third object of the invention is the identification of at least one epitope of M-CSF that is responsible for the biological activity of the molecule, which epitope is conformational in nature, being associated with dimeric, but not monomeric M-CSF.

A fourth object of the invention is a description of a method for monitoring refolding and restoration of biological activity of dimeric M-CSF from its corresponding monomers using monoclonal antibody that binds to an apparent conformational epitope present predominately on dimeric, but not monomeric M-CSF.

A fifth object of the invention is a description of a method of separating substantially active M-CSF from substantially inactive forms of the molecule by binding active M-CSF to monoclonal antibody that binds predominately to dimeric but not monomeric M-CSF.

A sixth object of the invention is a description of a method of separating substantially active chemically defivatized M-CSF from substantially inactive forms of the molecule by binding the defivatized molecule to monoclonal antibody that binds predominately to dimeric but not monomeric M-CSF.

These and other objects of the invention will become apparent upon reading the following disclosure of the invention.

DETAILED DESCRIPTION OF THE INVENTION

Because the instant invention concerns the generation of neutralizing monoclonal antibodies that recognize an apparent conformational epitope specific to dimeric M-CSF, a definition of M-CSF may facilitate an understanding of what applicants' invention encompasses. What applicants intend by referring to colony-stimulating factor, M-CSF, is a protein that exhibits the spectrum of biological activities commonly understood in the art to be associated with M-CSF, particularly as applied to the standard in vim colony-stimulating assay of Metcalf, D., *J. Cell Physiol* (1970) 76:89. In this assay M-CSF primarily results in the formation of macrophage colonies. There appears to be some species specificity: human M-CSF acts on both human and murine bone marrow cells; and murine M-CSF is not active on human cells. Additionally, other properties of M-CSF have been recognized more recently, and these include the ability of the protein to stimulate the secretion of alpha or beta interferon, intefieukin-2, interleukin-1, E series prostaglandin, and oxygen reduction products. Further, M-CSF also stimulates macrophage resistance to viral infection by vesicular stomatitis virus, and enhances the tumoricidal activity of macrophages under certain conditions. Although the mechanism(s) responsible for these activities is not at present understood, for the purposes of definition herein, the criteria for fulfillment of the definition resides in the ability of M-CSF to stimulate the formation of macrophage colonies using bone marrow cells from the appropriate species as starting materials.

In addition to being defined by its biological activities, M-CSF may also be defined in somewhat more general terms by its chemical structure. Unfortunately, however, the precise structure of naturally produced M-CSF is not clearly apparent from a reading of the scientific literature. For instance, human M-CSF purified from urine is thought to consist of two essentially identical subunits with apparent molecular weight of 25–35 kilodaltons. In contrast, M-CSF purified from a pancreatic carcinoma cell line, MIA PaCa-2, was reported to consist of two subunits, but with apparent molecular weights of about 23 kilodaltons. These differences may be due to differences in glycosylation, or may arise as a result of alternative splicing of M-CSF mRNA since it is known that there exists a common gene that encodes M-CSF which produces at least two differentially spliced mRNAs which produce different M-CSF protein precursors. The larger precursor is thought to give rise to a 70–90 kilodalton glycoprotein thought to be a dimer with 35–45 kilodalton subunits, possibly having about 223–224 amino acids. The smaller precursor yields a 40–50 kilodalton glycoprotein, also comprising a dimer with a subunit molecular weight of about 20–25 kilodaltons, and possibly with about 145–160 amino acids. Thus, it should be apparent that within the structural definition of M-CSF there exists a set of related proteins of varying molecular weights. It should be further apparent from the foregoing discussion that the definition of M-CSF is not restricted to proteins with the above-described molecular weights. It is to be anticipated, in light of the existence of multiple mRNAs coding for M-CSF, that proteins with molecular weights different from those discussed above will be discovered, and thus are intended to come within the definition of M-CSF.

It will further be appreciated with regard to the chemical structure of M-CSF, that its precise structure depends on a number of other factors. As all proteins contain ionizable amino and carboxyl groups it is, of course, apparent that M-CSF may be obtained in acidic or basic salt form, or in neutral form. It is further apparent, that the primary amino acid sequence may be augmented by derivatization using sugar molecules (glycosylation) or by other chemical derivatizations involving covalent, or ionic attachment to M-CSF with, for example, lipids, phosphate, acetyl groups and the like, often occurring through association with saccharides. These modifications may occur in vitro, or in vivo, the latter being performed by a host cell through post-translational processing systems. It will be understood that such modifications, regardless of how they occur, are intended to come within the definition of M-CSF so long as the activity of the protein, as defined above, is not destroyed. It is to be expected, of course, that such modifications to M-CSF may quantitatively or qualitatively increase or decrease the biological activity of the molecule, and such chemically modified molecules are also intended to come within the scope of the definition of M-CSF.

MODES FOR CARRYING OUT THE INVENTION

The invention consists of several aspects including 1) isolation of M-CSF, preferably recombinant M-CSF from either prokaryotes or eukaryotes, 2) immunization of a suitable host animal with M-CSF, 3) identification of monoclonal antibodies that recognize predominately dimeric, but not monomeric M-CSF, 4) utilization of those monoclonal antibodies that recognize dimeric M-CSF to assay for the formation of dimeric M-CSF in the presence of monomers, and 5) separation of biologically active dimeric M-CSF from substantially inactive monomeric forms of the molecule.

In addition, further aspects of the invention include methods whereby biologically active chemically derivatized dimeric M-CSF is separated from inactive forms of the molecule, and therapeutic and diagnostic applications involving sequestration of dimeric M-CSF using the monoclonal antibody. Each of the various aspects of the invention will be discussed separately.

Isolation Of M-CSF

M-CSF can be isolated from either natural sources, or from recombinant host cells that have been engineered to exhibit a DNA sequence that encodes M-CSF. Regarding isolating M-CSF from natural sources, Stanley, E. R., et at., *J Biol chem* (1977) 252:4305 describes the purification of a protein obtained from murine L929 cells that stimulates mainly macrophage production and has a specific activity of about $1\times10^8$ units/mg. Das, S. J., et al., *J. Biol. Chem.* (1982) 257:13679 reported that human urinary M-CSF has a specific activity of $5\times10^7$ units/mg and generates only macrophage cells. Stanley, E. R. and Gilbert, L. J., *Journal of Immunological Methods* (1981 ) 42:253 also describe methods for the purification of M-CSF in low yield. Das, S. K. et at., *Blood* (1981) 58:630 describe partial purification of human urinary M-CSF. Wu, N., et al., *J. Biol. Chem.* (1979) 254:6226 describe the purification of a M-CSF that primarily stimulates the formation of macrophages. More recently, M-CSF has been purified in milligram amounts using 10,000 liters of human urine as starting material.

In addition to the above references, there are numerous other reports that describe the purification and biological activity of colony-stimulating factors that have one or more of the properties ascribable to M-CSF. Motoyoshi, K. et. al., *Blood*, (1982) 60:1378 describe the colony-stimulating activity of a substance partially purified from normal human urine. Both granulocytes and macrophages are produced. Motoyoshi, J., et al., *Blood* (1978) 52:1012 also describe the purification and properties of a substance obtained from normal human serum having colony-stimulating activity. Stanley, E. R., et al., *Federal Proceeding* (1975) 2272 show the partial purification of a colony-stimulating factor from human urine that regulates granulopoiesis and macrophage production, while Wang, F. F. and Goldwasser, E., *Journal of Cellular Biochemistry* (1983) 21:263 show a 7-step procedure for purifying a M-CSF factor that is specific for the production of macrophages. Finally, U.S. Pat. No. 4,342,828, inventors Takaku, F. et al., shows the formation of human granulocytes from macrophages by a colony-stimulating factor obtainable from cultivated monocytes or macrophages isolated from human peripheral blood.

M-CSF may be obtained using the materials and methods described in the foregoing references and employed as immunogen to produce monoclonal antibodies that recognize dimeric forms of M-CSF. These references are hereby incorporated in their entirety.

Figure 1:
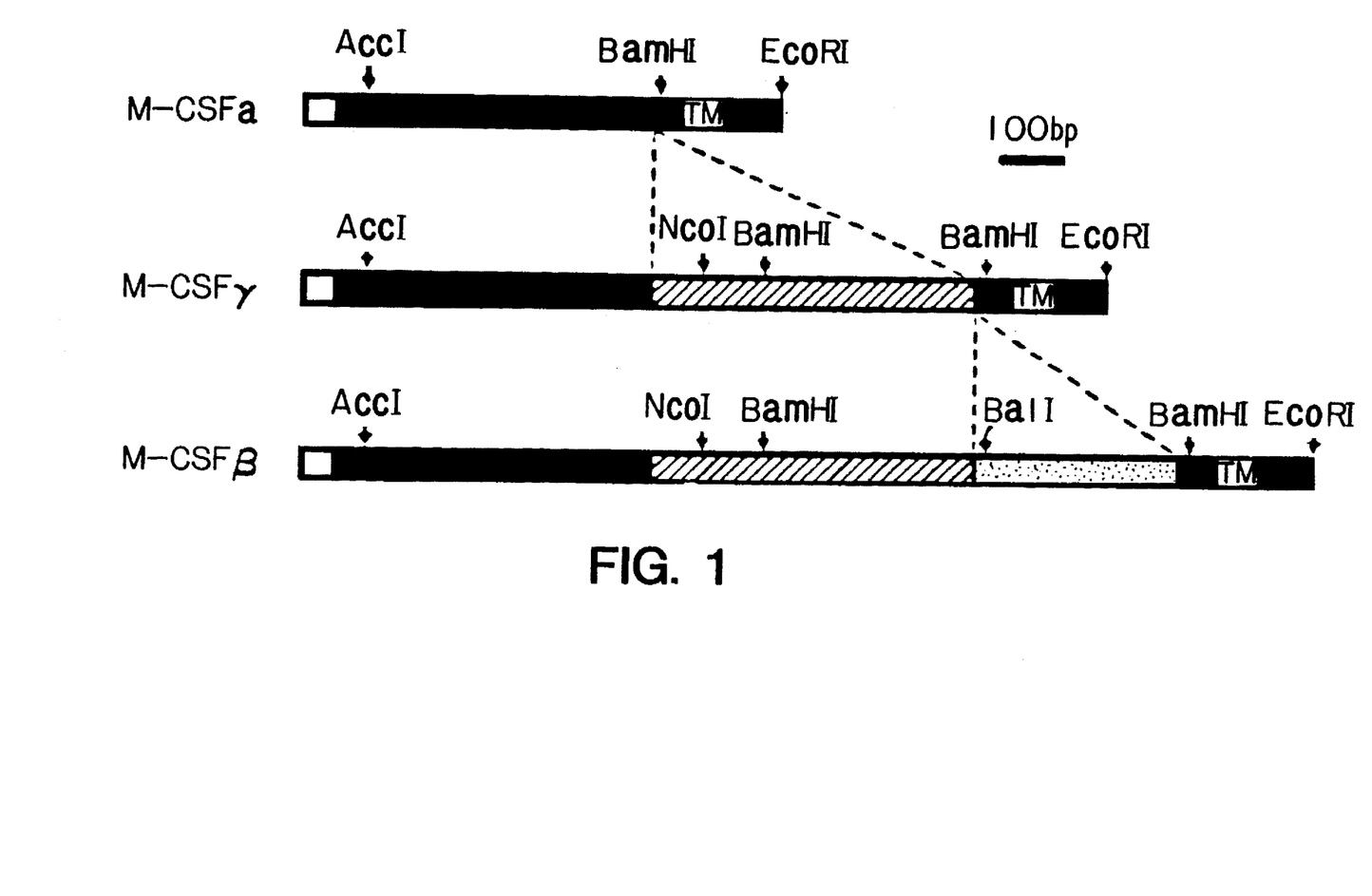
FIG. 1 shows restriction maps for human M-CSF cDNAs α, β and γ. Denoted are signal sequences (open boxes), transmembrane regions (TM), sequences common to the β and γ clones (striped boxes), and a sequence unique to the β clone (strippied box).

M-CSF has been cloned, and expressed in a number of host cells, and consequently, recombinant M-CSF (rM-CSF) is available for use as an immunogen to elicit antibodies. Indeed, to date, human rM-CSF (hrM-CSF) cDNA clones having three different lengths have been identified, herein denoted $\alpha$, $\beta$, and $\gamma$. They have been isolated from cells expressing the single M-CSF gene. The $\alpha$, $\beta$ and $\gamma$ clones contain M-CSF DNA sequences that encode unprocessed proteins having 224, 522 and 438 amino acids, respectively. The restriction maps of the various cDNAs are shown in FIG. 1.

Recombinant M-CSFs encoded by these clones have been expressed in active form, and thus these molecules may be used to generate suitable monoclonal antibodies. The preferred rM-CSF is that described in U.S. Pat. No. 4,847,201 inventors E. Kawasaki et al., filed Feb. 9, 1988. Therein is shown the expression, in both prokaryotes and eukaryotes, of the $\alpha$ form of M-CSF. This patent application, as well as the above references which show the $\beta$ and $\gamma$ forms of M-CSF, are hereby incorporated by reference in their entirety.

rM-CSF is produced in monomeric form in prokaryotes, such as *E. coli*, but is dependent on dimeric conformation for biological activity. Thus, if *E. coli* produced material is to be used as immunogen to generate monoclonal antibody it is preferably that the monomers be combined and refolded into the active dimeric form of M-CSF. rM-CSF monomers can be refolded as described below.

Because rM-CSF is recovered from *E. coli* as insoluble inclusion bodies, the monomers are first purified from the inclusion bodies using techniques known in the art, or by the following method. Inclusion bodies can be initially separated from cellular debris and solubilized in an effective solubilizing agent, such as urea. Additionally, the solution may contain metal ion chelators, and a reducing agent. The resulting solution is clarified, and monomeric M-CSF purified using techniques known in the art, preferably by high pressure liquid chromatography in the presence of a solubilizing agent, metal ion chelators and reducing agents. Chromatographic fractions are identified that contain monomeric M-CSF, and are concentrated, if required, to a concentration of about 5.0 mg/ml.

Monomeric M-CSF can be refolded preferably by diluting the solubilizing solution containing M-CSF, to an appropriate protein concentration, preferably 0.29–0.7 mg/ml into a buffered solution, pH of about 8.5, and containing an appropriate concentration of metal ion chelators. Additionally, the solution preferably contains a regenerative oxidation/reduction chemical system consisting of effective concentrations of reduced and oxidized glutathione to decrease the time that it takes to refold rM-CSF. More preferably, the system will consist of reduced and oxidized glutathione in a molar ratio of about 2:1. Refolding is permitted to occur over several days, and the extent and completion of refolding can be monitored by removing aliquots, reacting any unreacted SH groups with an appropriate blocking agent, and subsequently performing high pressure liquid chromatographic analysis on a suitable chromatographic matrix using a compatible buffer. It is noteworthy that refolding is preferably conducted at 4° C., although refolding can occur at higher temperatures such as 23°–37° C., albeit with a loss of yield.

Refolded M-CSF can be purified using a variety of purification techniques known in the art, preferably, however, hydrophobic interaction chromatography is employed. The materials and methods for carrying out hydrophobic chromatography are described generally by Shaltie, 1984, *Methods in Enzymology*, 104:69. It will be appreciated that there are many hydrophobic chromatographic materials and solid support matrices that may be used to purify M-CSF. The preferred hydrophobic chromatographic material is TSK-phenyl-5-PW, which is available from Bio-Rad. The purity and yield of refolded M-CSF can be determined using methods known in the art, including reduced and non-reduced sodium dodecyl sulfate polyacrylamide gel electrophoresis or high pressure liquid chromatography.

It is worth noting that M-CSF produced in prokaryotes, particularly *E. coli*, contains endotoxin that may be removed by the purification procedure chosen, otherwise endotoxin may adversely affect bioassays that may be employed to study the activity of M-CSF. In this regard, the purification procedures described above, readily reduces endotoxin concentrations to about 0.25 ng of endotoxin per mg M-CSF.

Immunization

Lymphocytes from a variety of species can be used to produce monoclonal antibody to dimeric M-CSF. Preferably, however, either murine or human lymphocytes will be used.

Murine hybridomas which produce monoclonal antibody to M-CSF can be formed by fusing mouse myeloma cells and immunized spleen cells, isolating fused hybrids, and identifying those that secrete monoclonal antibody. Preferably, mice are immunized with refolded dimeric M-CSF encoded by the M-CSF $\alpha$ cDNA clone, although it is to be anticipated that the refolded $\beta$ or $\gamma$ forms, or naturally occurring M-CSF will also induce antibody. To immunize mice, a variety of distinguishable immunization protocols may be employed. For instance, mice may be immunized intravenously, or intraperitoneally with a primary immunization followed by one or more boost. Alternatively, lymphocytes may be immunized in vitro. If mice are immunized, the precise immunization schedule is generally not critical, and determinative of which procedure is employed, is the presence of anti-M-CSF antibodies in mouse sera as measured by a M-CSF binding assay, described below.

Spleens from sera positive animals are removed, and the splenocytes therein used to prepare hybfidomas by fusion to a suitable myeloma cell line. The fusion is accomplished by standard procedures, such as that described by Kohler and Milstein, 1975, *Nature* (London), 256:495–497. Modifications to this procedure are known and practiced in the art. A variety of suitable myeloma lines are available from the American Type Culture Collection. The fusion technique involves fusing the myeloma cells and murine splenocytes using a suitable fusiongen, preferably polyethylene glycol. Following fusion, the cells are separated from the fusion medium and grown in a selective growth medium, such as HA or HAT medium, to kill off unhybridized parent cells.

Next, hybridomas supernatants are assayed for anti-M-CSF binding using any one of a number of conventional immuno-assay procedures (e.g., radio-immuno assay, enzyme immuno-assay, or fluorescent immuno-assay) using the immunizing agent, that is, M-CSF as antigen. Positive clones which secrete antibody that bind to M-CSF are characterized further to determine whether they recognize predominately dimeric M-CSF, and not monomers thereof.

A variety of such assays are available to distinguish antibody binding to M-CSF dimers versus monomers, and are known to those skilled in the art. One such assay is Western blotting wherein, M-CSF is subjected to sodium dodecyl sulphate (SDS) polyacrylamide gel electrophoresis under reducing, or nonreducing conditions, and blots prepared and probed as described by Burnette, 1981, *Anal. Bio. Chem.*, 112:195. The Western blots are blocked, washed, and probed preferably in 10 mM sodium phosphate buffer containing 150 mM sodium chloride (pH 7.4), with 0.1% bovine serum albumin (w/v), and 0.1% ovalbumin (w/v). In addition, a detergent is preferably employed such as Tween 20 at a concentration of about 0.1%. Sodium azide may also be included in the solution at a concentration of 0.02%. The blots are preferably first probed with either hybridoma culture supernatant, or dilute ascites fluid containing M-CSF antibody, washed, and then antibody binding revealed with $^{125}$I-protein A for about 30–60 minutes. The blots are washed, and subjected to autoradiography using X-ray film. The monoclonal antibodies from those hybridomas that recognize dimeric M-CSF are identified by radiolabelling of unreduced, but not reduced M-CSF.

Human hybridomas, which secrete antibody that recognize M-CSF dimers, may also be established. This is done, preferably, by fusing spleen cells from an individual immunized against M-CSF, and a suitable human lymphoblastoid cell fusion partner. An example of the latter is the cell line FB36, which is described in U.S. Pat. application Ser. No. 06/727,821, filed Apr. 26, 1985(now abandoned). Alternatively, in lieu of spleen cells as the fusion partner, human peripheral blood antibody-producing lymphocytes may be utilized. Immunization of peripheral blood cells may occur in vitro as described by Boss, in Methods of Enzymology, volume 121, part 1, and in EPA No. 86106791.6. The fusion and screening techniques used to identify human monoclonal antibodies that recognize M-CSF dimers are essentially the same as those used in the production and selection of murine hybridomas.

It will be appreciated by those skilled in the art that the foregoing methods exemplifying ways of obtaining and identifying the appropriate murine or human M-CSF monoclonal antibodies are merely representative of a number of such approaches that can be taken. For example, another method of forming anti-M-CSF antibody-producing cell lines that secrete antibody against M-CSF dimer, is by transformation of antibody-producing cells. These and other procedures are shown in *Methods of Enzymology*, Vol. 121 Part I. Note particularly in vitro immunization techniques that can be used to produced either murine or human monoclonal antibodies (Procedures for Transforming Cells, pages 18–32, 140–174). This publication is incorporated by reference in its entirety.

The instant monoclonal antibodies have multiple utilities. For instance, they may be used to separate biologically active dimeric M-CSF from monomeric M-CSF, as well as from dimeric forms of the molecule that have lost substantial biological activity arising from improper refolding of the molecule, or from chemical derivatization. The preferred application of the monoclonal antibody in these instances is to use it in an immuno-affinity column format.

It is important to note that because the monoclonal antibodies described herein bind to a conformational epitope on biologically active dimeric M-CSF, the antibody will show a lack of appreciable binding to biologically inactive or substantially inactive dimeric M-CSF provided that the loss of activity is attributable to an alteration of the epitope. Thus, with regard to chemical derivatization, the antibody will be most useful to separate chemically derivatized active dimeric M-CSF from inactive derivatized molecules. It will, of course, be understood by those skilled in the art that M-CSF may be derivatized notable using numerous reagents that are employed by scientists for various purposes. A notably derivatization reaction is conjugation of a water soluble polymer to M-CSF. Preferably the water soluble polymer is polyethylene glycol, or a functionally related molecule such as, for example, polypropylene glycol homopolymers, polyoxyethylated polyols, and polyvinyl alcohol. Derivatization of M-CSF with such water soluble polymers increases its in vivo half-life, reduces its immunogenicity, and reduces or eliminates aggregation of the protein and may reduce its immunogenicity and aggregation of that might occur when it is introduced in vivo. Derivatization of M-CSF with water soluble polymers such as those described are presented in U.S. Pat. No. 4,847,325, which application is hereby incorporated by reference in its entirety.

The following examples are illustrative of various ways in which the invention may be practiced. However, it will be understood by those skilled in the art that the presentation of such examples showing specific materials and methods is not meant to limit the invention in any way.

EXAMPLE I

Isolation/refolding of rCSF-1

Murine monoclonal antibody was generated against dimeric α-clone M-CSF. The molecule was produced, refolded, and purified as described in U.S. Pat. No. 4,847,201. Briefly, *E. coli* were transformed with a plasmid containing the α-clone of M-CSF and a *E. coli* cell paste was made therefrom by suspending the *E. coli* at an $OD_{680}$ of 84 in 6 ml of 50 mM Tris HCl, pH 8.5 containing 10 mM EDTA and lysing the cells by sonication. The lysate was centrifuged, and the resulting pellet resuspended in 2.5 ml of 30% sucrose containing 10 mM EDTA, pH 8.0. The inclusion bodies containing M-CSF were recovered by centrifugation of the sucrose solution at 10,000×g for 15 minutes, and solubilized in 8M urea, 50 mM Tris HCl, pH 8.5 containing 1 mM EDTA and 10 mM DTT for 30 minutes at room temperature. This solution, containing solubilized M-CSF was clarified by a further centrifugation step at 10,000×g for 10 minutes and filtration through a 0.45 micron filter. Finally, M-CSF monomer was purified by size exclusion high pressure liquid chromatography on a Bio-Sil® TSK-250 column (21.5×600 mm) previously equilibrated with 8M urea, 0.1M sodium phosphate buffer, 1 mM DTI and 1 mM EDTA. Monomeric M-CSF accounted for the major protein peak detected, and fractions comprising this peak were pooled and concentrated to 5.0 mg/ml with an Amicon stirred cell using a YM-10 membrane.

M-CSF monomer, isolated as described above, was refolded as follows. The monomer was diluted to a protein concentration of either 0.3 or 0.7 mg/ml in pre-cooled 50 mM Tris HCl buffer, pH 8.5 containing 5 mM EDTA, 2 mM reduced glutathione, and 1 mM oxidized glutathione. This mixture was incubated for four days at 4° C. to permit maximum refolding of monomers into dimeric M-CSF. The refolding reaction was followed by removing aliquots from the mixture, blocking unreacted sulfhydryl groups with iodoacetamide (50 mM concentration), freezing the samples at −70° C., and subjecting thawed samples to size exclusion high pressure liquid chromatographic analysis using a TSK-G3000SWXL column (available from Varian Associates). The latter column was pre-equilibrated with 10 mM sodium phosphate buffer pH 6.8, containing 150 mM sodium chloride.

At the end of the refolding period, M-CSF was dialyzed for 18 hours at 4° C. in 0.1M sodium phosphate pH 7.0, to remove residual glutathione. Next, ammonium sulfate was added to the refolded mixture to a concentration of 1.2M, and the pH of the solution was adjusted to 7.0, and the mixture loaded onto a depyrogenated Bio-Rad TSK-phenyl-5-PW column (7.5×75 mm) previously equilibrated in 1.2M ammonium sulfate, 0.1M sodium phosphate, pH 7.0. Finally, M-CSF was eluted from the column with a 45 minute crisscrossing gradient of decreasing ammonium sulfate and increasing ethylene glycol (buffer B=30% ethylene glycol, 0.1M sodium phosphate, pH 7.0). Lastly, those fractions containing purified M-CSF were pooled, dialyzed into 1% mannitol containing 10 mM sodium phosphate, 150 mM sodium chloride, pH 7.4, filter sterilized, and stored at 4° C. until such time as material was used to immunize mice. To eliminate or reduce endotoxin present in the M-CSF preparation, all buffers were prepared using depyrogenated water and glassware.

EXAMPLE II

Immunization/Antibody Production

Balb/c mice were immunized with the above refolded rM-CSF. Immunization consisted of an primary intraperitoneal immunization of 40 µg of rM-CSF in complete Freunds adjuvant, followed by two subsequent intraperitoneal injections without complete Freunds adjuvant, consisting of 20 µg M-CSF each. The first immunization consisting of 20 µg was administered about three weeks after the primary immunization, and the 2nd 20 µg boost was administered about one week later. About five and one half weeks after the second 20 µg boost, a final immunization was conducted consisting of administering 10 µg of M-CSF intravenously. Three days later spleens from immunized mice were removed, and the splenocytes fused to a murine myeloma cell line.

The fusion procedure that was followed is described by Kohler & Milsrein, 1975, *Nature*, 256:495, as modified by Fendly et al., in *Hybridoma*, 6:359 (1987). Briefly, mice were sacrificed and splenocytes teased from immunized spleens, and washed in serum free Dulbecco's Modified Eagles medium. Similarly, SP²/0Ag14 myeloma cells were washed, and combined with the splenocytes in a 5:1 ratio, spleen cells to myeloma cells. The cell mixture was pelleted, media removed and fusion affected by the addition of 1.0 ml of 40% (v/v) solution of polyethylene glycol 1500 by dropwise addition over 60 seconds at room temperature, followed by a 60 second incubation at 37° C. To the cell suspension with gentle agitation was added 9 ml of Dulbecco's Modified Eagles medium over 5 minutes. Cell clumps in the mixture were gently resuspended, the cells washed to remove any residual PEG and plated at about $2\times10^5$ cells/well in Dulbecco's Modified Eagles medium supplemented with 20% fetal calf serum. After 24 hours, the cells were fed a 2× solution of hypoxanthine and azaserine selection medium. The cells were plated in a total of 15.5 microliters plates, which corresponds to 1488 wells. Subsequently, about 2.4 weeks later 684 wells exhibited good cell growth, and these were screened for antibody to M-CSF.

EXAMPLE III

Anti body Specificity

Hybridoma supernatants were screened initially for production of antibody to M-CSF using an immunoprecipitation assay, and subsequently rescreened using Western blotting techniques to determine if they recognized either monomeric and/or dimeric forms of the molecule. The initial screen consisted of mixing 50 gl of hybridoma culture supernatants with about $10^5$CPM/well of $^{125}$I labelled refolded *E. coli* M-CSF for about 1 hour at room temperature. Subsequently, a second antibody, rabbit anti-mouse conjugated to immunobeads (Bio-Rad) was added to the wells and incubated for an additional hour. This time period permits efficient binding of the rabbit antibody to any mouse antibody present in the culture supernants. Next, unbound $^{125}$I M-CSF was =removed by centrifugation, followed by washing the immunobeads containing bound anti-M-CSF antibody. The beads were washed three times, and the wells containing the beads were cut out, and counted using a γ-counter. From the 684 wells which exhibited positive hybridoma cell growth, only three yielded hybrids that secreted antibody to *E. coli* M-CSF. These hybridomas were denoted 382-4, 382-3F1, and 382-4B5. 382-5H4 was subcloned, and a resulting subclone was used for further studies, and is denoted 382-5H4 1A8 1F6. 382-3F1 and 382-4B5 were not extensively characterized because they produced low titers of antibody. The hybridoma producing monoclonal antibody 382-5H4 1A8 1F6 was deposited with the American Type Culture Collection, 12301 Parklawn Drive, Rockville, Md. 20852-1776, on Feb. 3, 1989 under the accession number HB10027. The hybridoma has been deposited with the Cetus Tissue Culture Collection with the Deposit Number 10523.

Figure 2A:
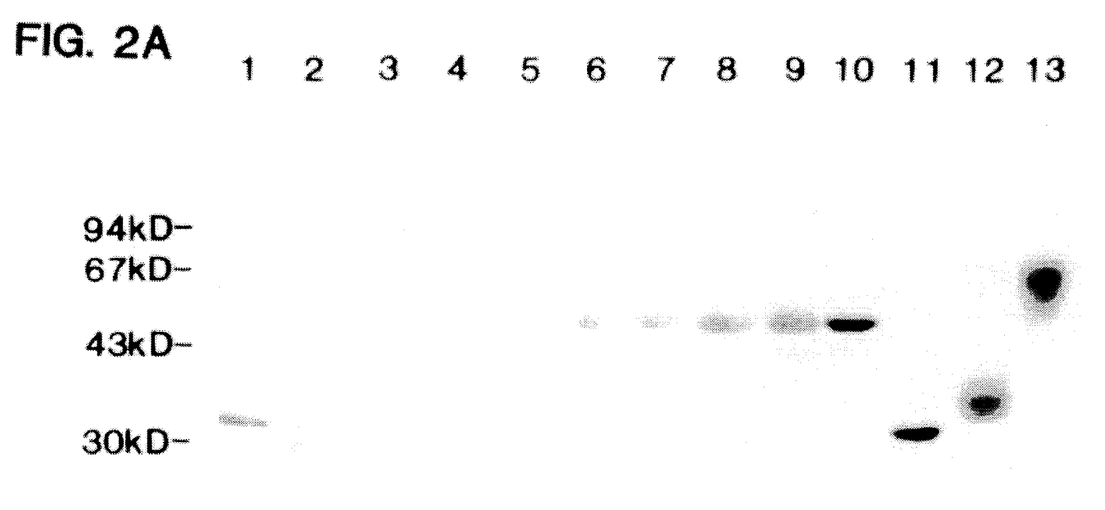
FIG. 2A and FIG. 2B show Coomassie staining and Western blotting results, respectively, of refolded rM-CSF at various times during the refolding reaction using the monoclonal antibody 382-5H4 1A8 1F6 to detect dimeric rM-CSF.
Figure 2B:
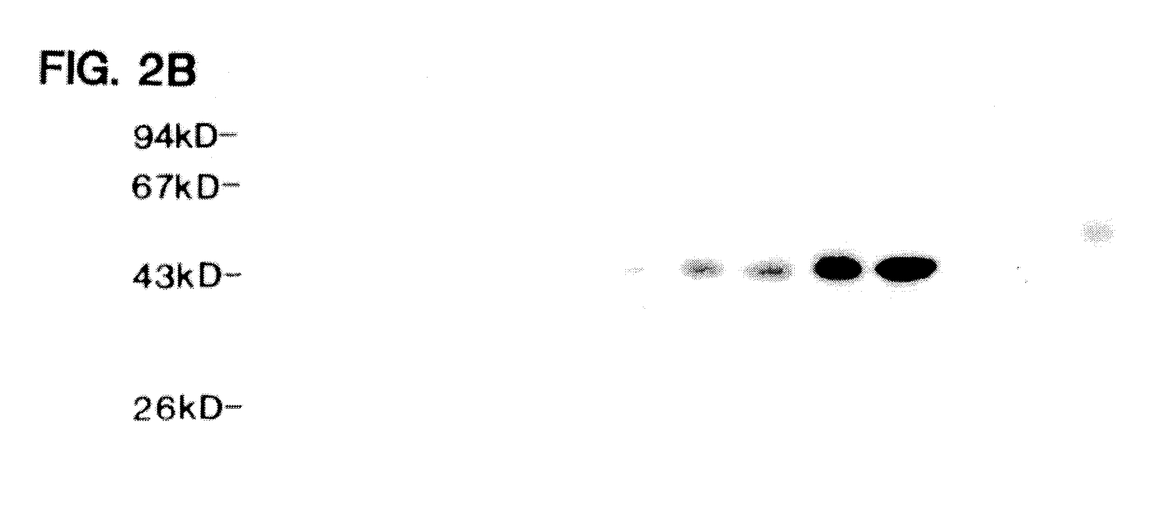

The epitope specifity of 382-5H4 1A8 1F6 was assessed on refolded rM-CSF using Western blotting techniques to determine whether it bound to either rM-CSF monomers, dimers, or both. Aliquots of refolded material were removed at various times during the refolding reaction, and either reduced (10 mM DTT, while boiling the samples) and blocked with 50 mM iodoacetamide, or blocked but not reduced, and subsequently electrophoresed as described by Laemmli, 1970, *Nature*, 237:680. Electrophoresis was conducted using 10% gels. The blotting method followed is described by Burnette, 1981, *Anal. Biol. Chem.*, 112:195. Both reduced and unreduced M-CSF were blotted onto nitrocellulose, and probed with the monoclonal antibody, and revealed with $^{125}$I-protein A. FIG. 2B shows the autoradiographic results, while FIG. 2A shows corresponding Coomassiee Blue staining profiles. Samples in lanes 1–10, and 13 were run under non-reducing/blocked conditions. Samples in lanes 12, and 11 were reduced/blocked. Lane 1 shows an aliquot of M-CSF from a 0.3 mg/ml refolding reaction takes at time 0 of the reaction, that is, immediately after initiation of refolding. Lanes 2–8 show refolded samples taken at 15, 60 minutes, 3, 6, 17, 25, and 96 hours, respectively. Lane 9, shows 0.7 mg/ml M-CSF refolding at time 96 hours. Lanes 10 and 11 show refolded M-CSF protein after phenyl-HPLC purification. It is apparent from the figure that the monoclonal antibody (382-5H4 1A8 1F6) reacts with unreduced, that is dimeric M-CSF as revealed by the labelling of protein present in Lanes 4–8 at the molecular weight expected for dimeric M-CSF. It is further apparent that the antibody does not show substantial reactivity to the monomeric form of the molecule as revealed by the absence of labelling of the M-CSF monomer in Lanes 1–6, which contain significant mounts of monomer.

Figure 3:
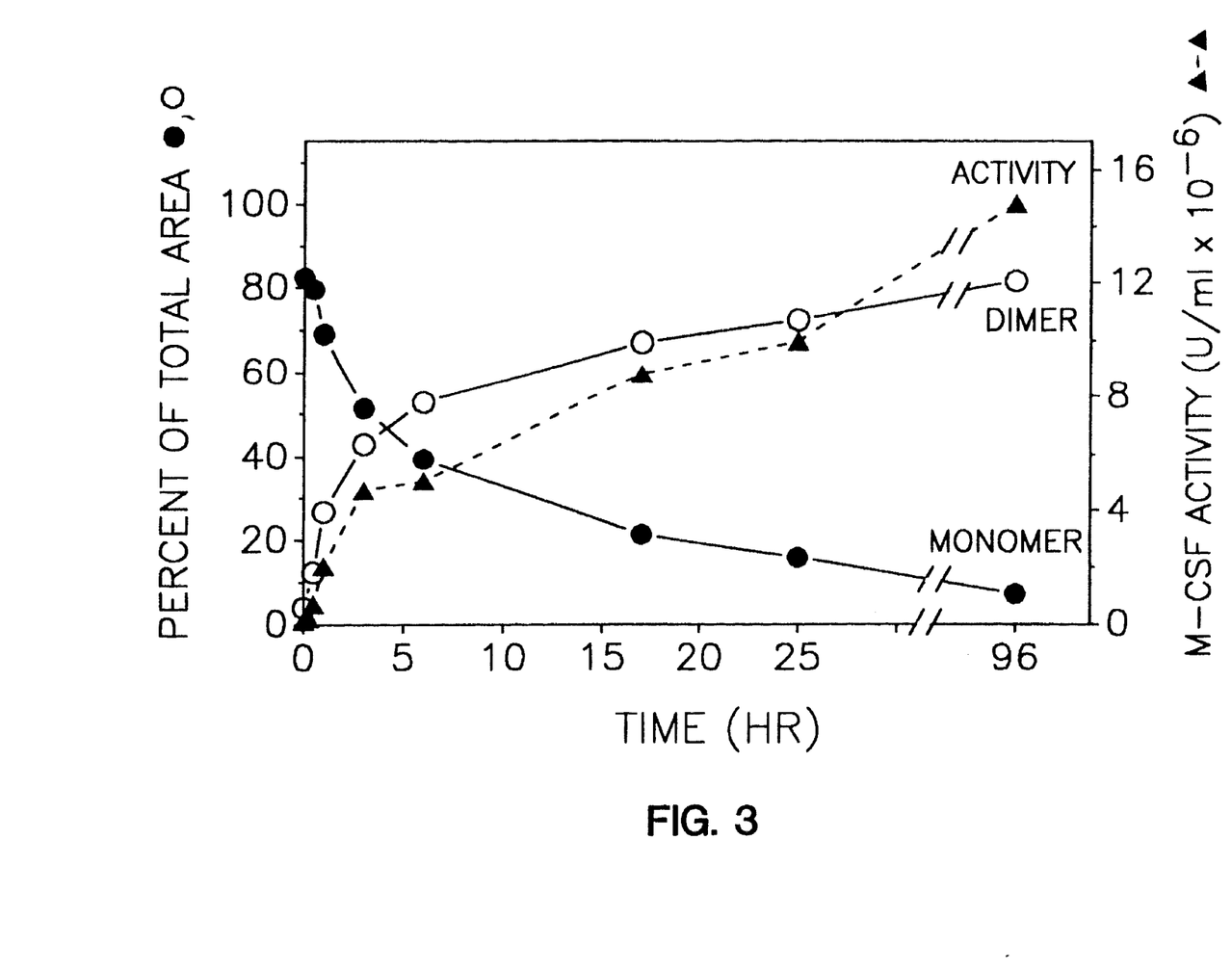
FIG. 3 correlates M-CSF dimer formation with bioactivity.

The conversion of M-CSF monomers into dimers was quantitated by measuring the area of each species resolved by non-denaturing SEC-HPLC. FIG. 3 shows that M-CSF bioactivity correlates with refolding of monomers into the dimeric form of the molecule. M-CSF activity was measured using the monocyte M-CSF dependent cell line proliferation assay described above.

A second assay was conducted to demonstrate that 382-5H4 1A8 1F6 bound to dimeric but not to monomeric M-CSF in solution. This consisted of performing the following immuno-precipitation experiment. Sixteen µl aliquots of the samples taken during the refolding reaction of Example III (blocked with iodoacetamide, as described above), were mixed with 10 µl of the 382-5H4 1A8 1F6 monoclonal antibody in phosphate-buffered saline (PBS) and held overnight at 4° C. Twenty µl of a 50% slurry of protein A-Sepharose (Pharmacia) was added to each sample held for two hours at 4° C., and then washed twice with PBS and centrifugation. M-CSF protein was eluted from the beads by boiling in SDS-sample buffer containing iodoacetamide and then subjected to SDS-PAGE analysis and Coomassie staining. As a positive control, a polyclonal antibody to M-CSF (described in U.S. Pat. No. 4,847,325, filed Jan. 20, 1988) that detects both monomeric and dimeric forms of M-CSF was also used to immunoprecipitate the refolded samples. None of the partially folded, monomeric forms of M-CSF were precipitated from the refolding reaction by the monoclonal antibody; only the dimeric forms were detected. The control antibody precipitated both the monomeric and dimeric forms of M-CSF from these refolding samples, as expected. These results demonstrate that the monoclonal antibody 382-5H4 1A8 1F6 is specific for only dimeric forms of M-CSF in solution.

382-5H4 1A8 1F6 was isotyped using standard techniques known to those skilled in the an and determined to be of the IgG 1 class.

EXAMPLE IV

Neutralizing Activity

The capacity of 382-5H4 1A8 1F6 to neutralize the biological activity of M-CSF was determined. The assay is based on the inhibition of M-CSF stimulated cell proliferation of a mouse monocyte cell line. M-NFS-60 is a murine retrovirus-transformed myeloid leukemia cell line that was initially selected for growth in M-CSF and derived from NFS-60, a cell line described by Weinstein, et al., 1986, *Proc. Natl. Acad. Sci. USA*, 83:5010. M-NFS-60 is on deposit with the Cetus Tissue Culture Collection with Deposit No. 10523.

The assay was conducted in RPMI 1640 medium without fetal bovine serum, but containing 1% penicillin/streptomycin, 0.05 mM 2-mercaptoethanol, 2 mM glutamine, and with or without approximately 1,000 mouse bone marrow colony forming units/ml of M-CSF. The latter can be recombinant human M-CSF, or with cell conditioned medium which contains murine M-CSF.

To determine the neutralizing titer of the 382-5H4 1A8 1F6 MAb against native and recombinant M-CSF, the following assay was performed. Recombinant M-CSF produced in *E. coli* or CHO cells, as described above, or native M-CSF from MIA PaCa cells (partially purified), was diluted into tissue culture medium to a final concentration of approximately 4000 U/ml. A 1/2 dilution of each of the M-CSFs was done into tissue culture medium to a final concentration of approximately 2000 U/ml. Next, a 1/100 dilution of an ascites preparation of the 382-5H4 1A8 1F6 MAb was prepared in tissue culture medium. 150 µl of the diluted antibody was mixed with 150 µl of the 4000 U/ml M-CSF stock solution, each type of M-CSF being assayed separately. Each of these samples were vortexed and then 150 µl was withdrawn and added to 150 µl of the corresponding 2000 U/ml solutions of M-CSF. After vortexing, 150 µl was withdrawn and added to another 150 µl aliquot of the 2000 U/ml M-CSF stock solutions. This step was repeated six more times. In this manner, the monoclonal antibody was serially diluted out in a constant amount of recombinant or native M-CSF over a dilution range from 1/200 to 1/51200. These samples were held overnight at 4° C. and then tested for M-CSF stimulatable M-NFS-60 cell growth activity. To 50 µl of the appropriate antibody/M-CSF dilution was added 50 µl of assay medium and 50 µl containing about $5 \times 10^3$ cells. This mixture was then added to microtiter tissue culture wells, and the cells incubated for 48 hours at 37° C. in an atmosphere of 5% $CO_2$/95% air.

After the 48 hour incubation period, cell number was assessed using (3-[4,5-Dimethylthiazol-2-yl]-2,5-Biphenyltetrazolium bromide) (MTT). A stock solution of MTT was made up at a concentration of 5 mg/ml in phosphate buffered saline, and prior to use filtered through a 0.2 µ filter, and stored at 4° C. in a light-proof box. The MTT solution was warmed to 37° C., and 25 µl added per well subsequent to shaking the microtiter plates for 3–5 minutes on a microplate shaker at 700 revolutions per minute. The plates were incubated for 3 hours at 37° C., again in an atmosphere of 5% $CO_2$/95% air, followed by removing the plates from the incubator, agitating them on a microplate shaker for 3–5 minutes at 700 revolution per minute, and adding 100 µl of a MTT solubilizing solution consisting of 20% sodium dodecyl sulfate (wt./vol.) in water. The wells were mixed, and after sitting at room temperature for several hours, the $OD_{570}$ nm determined.

From these results, the capacity of the monoclonal to inhibit M-CSF M-NFS-60 stimulated cell growth was determined, and the neutralizing liter of the ascites preparation of this monoclonal antibody was determined. The 382-5H4 1A8 1F6 MAb displayed an essentially equivalent neutralizing liter against all three forms of M-CSF tested, having a titre of approximately $4 \times 10^7$ neutralizing units per ml of ascites fluid.

A second assay may be used to assess the neutralizing activity of the antibody based on its capacity to inhibit mouse bone marrow colony formation. It is described by Metcalf, J., 1970, *Cell Physiol.*, 76:89.

Regardless of which assay is performed, M-CSF activity may be standardized using purified M-CSF from MIA PaCa-2 cell supernatants. The MIA PaCa-2 standard was quantitated by repeatedly measuring its activity in the mouse bone marrow colony-forming assay. MIA PaCa-2 is a pancreatic carcinoma cell line available from the American Type Culture Collection, Accession No. CRL140, and M-CSF can be isolated from culture supernatants as described by Boosman, et al., 1987, *Biochem. Biophys. Res. Com.*, 141:74.

EXAMPLE V

Antibody Cross Reactivity

The capacity of 382-5H4 1A8 1F6 to cross-react with rM-CSF produced in mammalian cells was determined. Two mammalian expressions systems were used. M-CSF was expressed in COS cells, more specifically, CV-1 cells as described by Weaver, et at., 1988, *Bio. Tech.*, 6:287. In this system, the α M-CSF cDNA clone encoding rM-CSF is present in a plasmid, pCSF-17 (described in U.S. Pat. No. 4,847,201), which is stably integrated into CV-1 cells. rM-CSF is expressed in this system when CV-1 cells are provided with SV40 T antigen. T antigen affects the replication and expression of pCSF-17, causing a transient rise in plasmid copy number, and a concomitant increase in the expression of rM-CSF. rM-CSF was isolated from the cell culture media using standard techniques.

M-CSF was also expressed in a second mammalian system, that is Chinese hamster ovary (CHO) cells as described by Wong et al., in Science, page 1504, volume 235, (1987). In this system, full length M-CSF encoded by the M-CSF cDNA clone is expressed. The cells are grown in standard cell culture media, and the M-CSF secreted therein purified as follows. The cell culture supernatant was first dialyzed and applied to a Zeta prep anion exchange column and then purified by DEAE-HPLC chromatography using a Bio-Rad TSK DEAE-5-PW column (21.5×150 mm). Protein was loaded onto the column in 30 mM Tris HC1, pH 8.5, and eluted with a 45-minute, 0–0.6M sodium chloride gradient. Those fractions enriched for M-CSF were identified, pooled and ammonium sulfate added to 1.2M. The final pH of the solution was 7.0. This material was then purified using hydrophobic interaction chromatography and formulated as described in Example I for the *E. coli* produced M-CSF. FIG. 1A, Lanes 13 and 14 show purified CHO M-CSF.

The capacity of the 382-5H4 1A8 1F6 to neutralize rM-CSF produced in CV-1/SV-40, or CHO was conducted as described in the preceding examples using the monocyte cell assay. The data showed that 382-5H4 1A8 1F6 completely neutralized M-CSF activity in both systems.

Further studies were undertaken to elucidate additional activities of the 382-5H4 1A8 1F6 antibody. The capacity of the monoclonal antibody to precipitate mammalian expressed M-CSF was determined. Using the immunoprecipitation techniques described in Example I, it was ascertained that 382-5H4 1A8 1F6 precipitates M-CSF produced in CV-1 cells.

EXAMPLE VI

Separation of Derivatized M-CSF

It will be appreciated that the instant monoclonal antibody can be employed to separate virtually all biologically active chemically deñvatized dimeric forms of M-CSF from monomeric M-CSF, or from inactive improperly folded forms of the molecule that result from the derivatization process. A preferred embodiment of this application is the separation of biologically active polyethyleneglycol (PEG) derivatized M-CSF, pegylated M-CSF, from other species of M-CSF present in the reaction mixture, including monomeric M-CSF, with or without PEG attached, and biologically inactive pegylated dimeric M-CSF.

M-CSF can be pegylated as described in U.S. Pat. No. 4,847,325. The reaction can be conducted under conditions whereby one or more PEG molecules is bound per M-CSF (i.e.M-CSF PEG 1-mer, 2-mer etc.). Preferably, one mole of PEG will be bound per mole of M-CSF. In this instance, the antibody can be used in an essential single step process to separate pegylated active M-CSF from the other reactants since there will be little non-pegylated M-CSF to compete for antibody binding. The reaction mixture can be chromatographed using an 5H4 1A8 1F6 immuno-affinity column as described in the preceding example. Alternatively, pegylated M-CSF may first be purified to obtain a substantially homogenous preparation of 1-mer, and this preparation subjected to immuno-affinity chromatography using the instant monoclonal antibody to produce an enriched population of biologically active dimeric 1-mer.

Despite the fact that the foregoing invention has been described in some detail by way of example, it will be apparent to those with ordinary skill in the an that various changes and modifications may be substituted for those shown in the examples, and that the scope of the patent application should not be construed as being limited other than by the appended claims.

What is claimed:

1. A mouse monoclonal antibody that:
   a) specifically binds to an epitope on dimeric, human M-CSF which is recognized by monoclonal antibody 382-5H4 1A8 1F6 secreted by a hybridoma on deposit with the American Type Culture Collection with Accession Number HB10027;
   b) does not measurably bind to monomeric human M-CSF; and
   c) neutralizes the biological activity of human M-CSF as determined by the ability of the monoclonal antibody to inhibit M-CSF bioactivity in vitro.

2. The monoclonal antibody as described in claim 1, wherein said antibody binds to M-CSF encoded by alpha, beta, or gamma M-CSF cDNA clones.

3. The monoclonal antibody of claim 1, wherein said monoclonal antibody does not bind to biologically inactive dimeric, human M-CSF.

4. Monoclonal antibody 382-5H4 1A8 1F6 secreted by a hybridoma on deposit with the American Type Culture Collection with Accession Number HB10027.

5. A hybridoma which secretes the monoclonal antibody as described in claim 1.

6. A hybridoma which secretes the monoclonal antibody, as described in claim 3.

7. A hybridoma which secretes monoclonal antibody 382-5H4 1A8 1F6, said hybridoma on deposit with the American Type Culture Collection, with Accession Number HB10027, and with the Cetus Tissue Culture Collection with Deposit Number 10523.

8. A method for determining the presence of human M-CSF dimers in solution, comprising the steps of:
   a) contacting said solution with said monoclonal antibody of claim 1, thereby forming a complex comprising said monoclonal antibody and M-CSF dimers; and
   b) isolating and revealing said complex.

9. A method as described in claim 8, further including the step of Separation of M-CSF monomers and dimers prior to step (a).

10. A method as described in claim 9, wherein said separation of monomers and dimers is by electrophoresis.

\* \* \* \* \*